United States Patent
Prevost et al.

(10) Patent No.: US 9,681,961 B2
(45) Date of Patent: Jun. 20, 2017

(54) SURGICAL INSTRUMENT SYSTEM AND METHOD

(71) Applicant: Warsaw Orthopedic, Inc., Warsaw, IN (US)

(72) Inventors: Julien J. Prevost, Memphis, TN (US); David Browning, Cordova, TN (US); Aubrey R. Mills, Memphis, TN (US); Eric A. Potts, Indianapolis, IN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 362 days.

(21) Appl. No.: 14/450,038

(22) Filed: Aug. 1, 2014

(65) Prior Publication Data

US 2016/0030195 A1 Feb. 4, 2016

(51) Int. Cl.
*A61F 2/46* (2006.01)
*A61F 2/44* (2006.01)
*A61F 2/30* (2006.01)

(52) U.S. Cl.
CPC .............. *A61F 2/4611* (2013.01); *A61F 2/44* (2013.01); *A61F 2002/3055* (2013.01); *A61F 2002/30507* (2013.01); *A61F 2002/30523* (2013.01); *A61F 2002/30601* (2013.01); *A61F 2002/30617* (2013.01); *A61F 2002/4627* (2013.01); *A61F 2002/4642* (2013.01); *A61F 2002/4658* (2013.01)

(58) Field of Classification Search
CPC .................. A61F 2/4611; A61F 2002/4627
See application file for complete search history.

(56) References Cited

U.S. PATENT DOCUMENTS

| | | | |
|---|---|---|---|
| 5,989,290 A | 11/1999 | Biedermann et al. | |
| 6,015,436 A | 1/2000 | Schoenhoeffer | |
| 6,176,881 B1 | 1/2001 | Schaer et al. | |
| 6,193,756 B1 | 2/2001 | Studer et al. | |
| 6,866,682 B1 | 3/2005 | An et al. | |
| 6,908,485 B2 | 6/2005 | Crozet et al. | |
| 7,674,296 B2 | 3/2010 | Rhoda et al. | |
| 7,811,327 B2 | 10/2010 | Hansell et al. | |
| 8,062,366 B2 | 11/2011 | Melkent | |
| 8,083,780 B2 | 12/2011 | McClellan, III | |
| 8,152,852 B2 | 4/2012 | Byani | |
| 8,182,535 B2 | 5/2012 | Kraus | |
| 2004/0153158 A1* | 8/2004 | Errico | A61F 2/442 623/17.14 |
| 2005/0033305 A1* | 2/2005 | Schultz | A61F 2/4425 606/99 |
| 2005/0143749 A1* | 6/2005 | Zalenski | A61F 2/4611 606/99 |
| 2006/0030856 A1* | 2/2006 | Drewry | A61B 17/025 606/90 |

(Continued)

*Primary Examiner* — David Bates

(57) ABSTRACT

A surgical instrument includes a body extending between a first end and a second end and includes at least one mating element engageable with an interbody implant. A first member is disposed with the body and engageable with the interbody implant to move the interbody implant between a first configuration and a second, expanded configuration. A second member is disposed with the body and engageable with the interbody implant to fix the interbody implant in a selected second configuration. Systems and methods are disclosed.

20 Claims, 17 Drawing Sheets

(56) References Cited

U.S. PATENT DOCUMENTS

| | | | |
|---|---|---|---|
| 2006/0111784 A1* | 5/2006 | Grinberg | A61F 2/0095 623/17.15 |
| 2007/0162128 A1* | 7/2007 | DeRidder | A61F 2/4465 623/17.11 |
| 2008/0140204 A1* | 6/2008 | Heinz | A61F 2/4425 623/17.16 |
| 2008/0188941 A1* | 8/2008 | Grotz | A61F 2/4611 623/17.16 |
| 2008/0287957 A1* | 11/2008 | Hester | A61B 17/025 606/99 |
| 2009/0112324 A1* | 4/2009 | Refai | A61F 2/44 623/17.11 |
| 2009/0192611 A1* | 7/2009 | Lindner | A61F 2/44 623/17.11 |
| 2011/0178598 A1 | 7/2011 | Rhoda et al. | |
| 2011/0251692 A1 | 10/2011 | Mclaugilin et al. | |
| 2012/0265303 A1* | 10/2012 | Refai | A61F 2/44 623/17.11 |

* cited by examiner

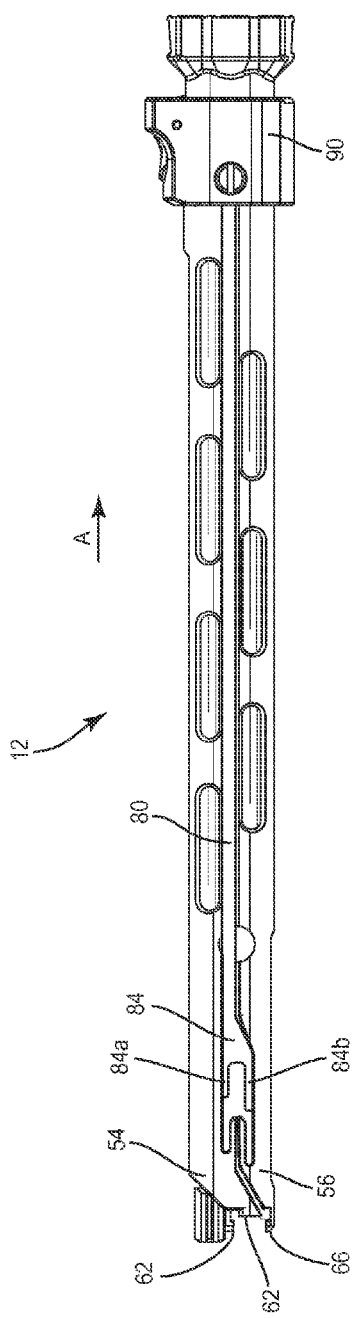
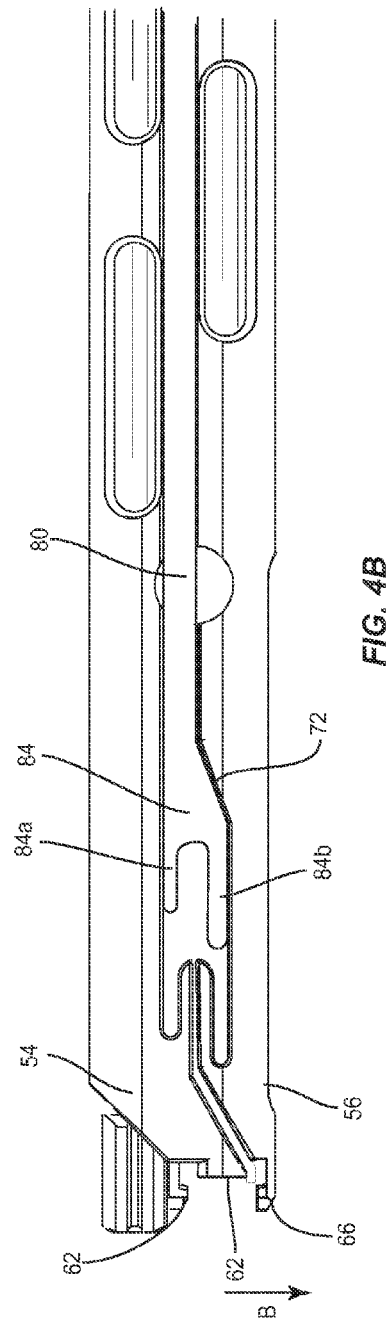
FIG. 4A
FIG. 4B

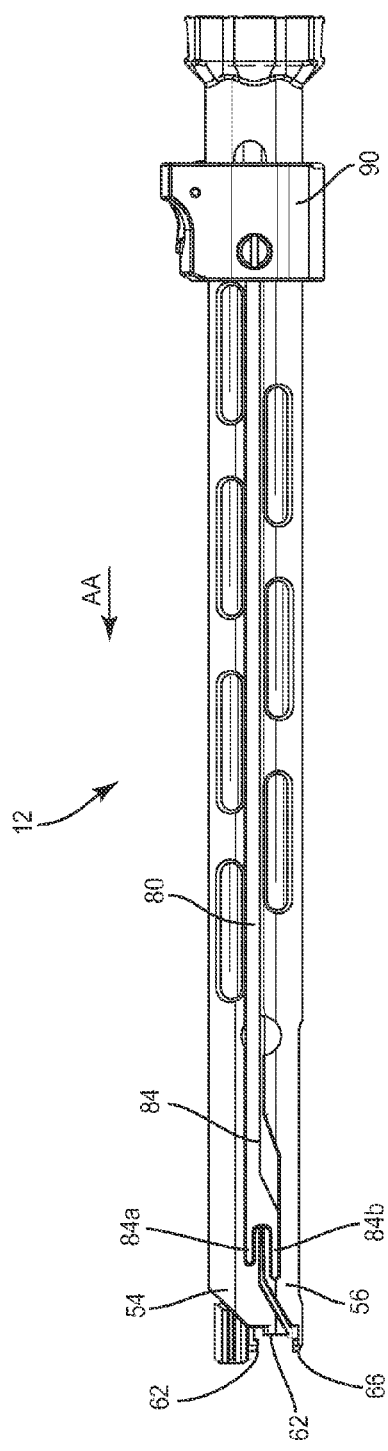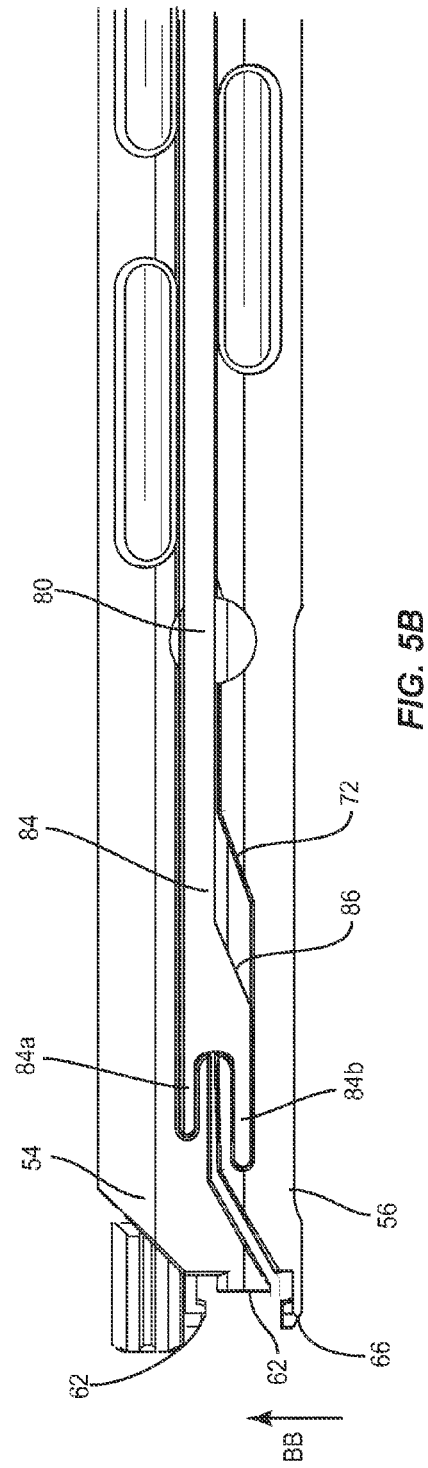
FIG. 5A
FIG. 5B

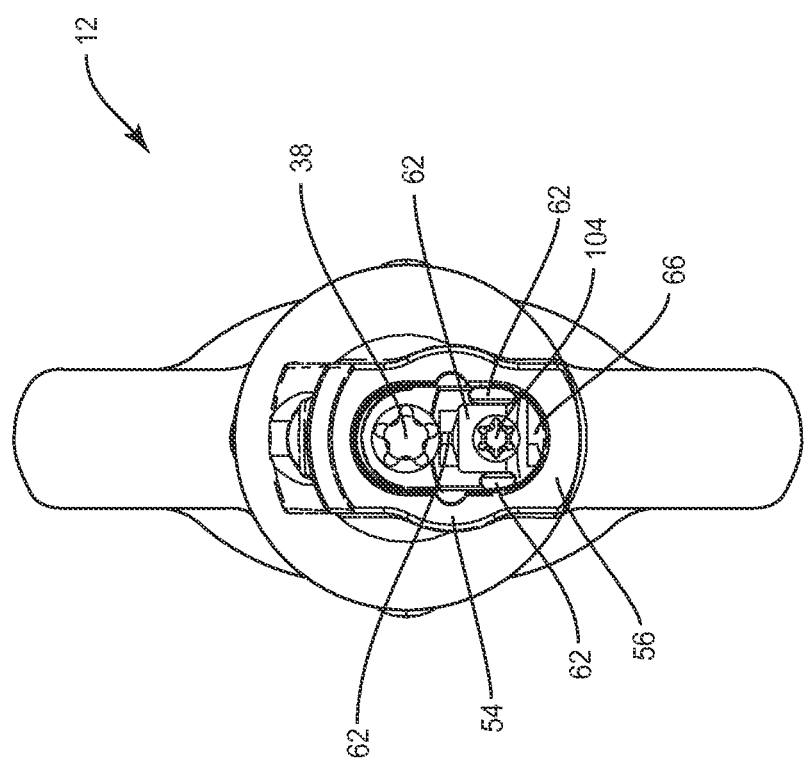

SURGICAL INSTRUMENT SYSTEM AND METHOD

TECHNICAL FIELD

The present disclosure generally relates to medical devices for the treatment of musculoskeletal disorders, and more particularly to a surgical system for delivering a spinal implant with a surgical site and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. In procedures, such as, for example, corpectomy and discectomy, fusion and fixation treatments may be performed that employ implants to restore the mechanical support function of vertebrae. Surgical instruments are employed, for example, to engage the implants for disposal at a surgical site. This disclosure describes an improvement over these prior art technologies.

SUMMARY

In one embodiment, a surgical instrument is provided. The surgical instrument includes a body extending between a first end and a second end and includes at least one mating element engageable with an interbody implant. A first member is disposed with the body and engageable with the interbody implant to move the interbody implant between a first configuration and a second, expanded configuration. A second member is disposed with the body and engageable with the interbody implant to fix the interbody implant in a selected second configuration. Systems and methods of us are disclosed.

BRIEF DESCRIPTION OF THE DRAWINGS

The present disclosure will become more readily apparent from the specific description accompanied by the following drawings, in which:

FIG. 4a is a side view of components of the system shown in FIG. 1;

FIG. 4b is an enlarged break away view of the components shown in FIG. 4a;

FIG. 5a is a side view of components of the system shown in FIG. 1;

FIG. 5b is an enlarged break away view of the components shown in FIG. 5a;

FIG. 6 is an axial view of components of the system shown in FIG. 1;

DETAILED DESCRIPTION

Figure 1:
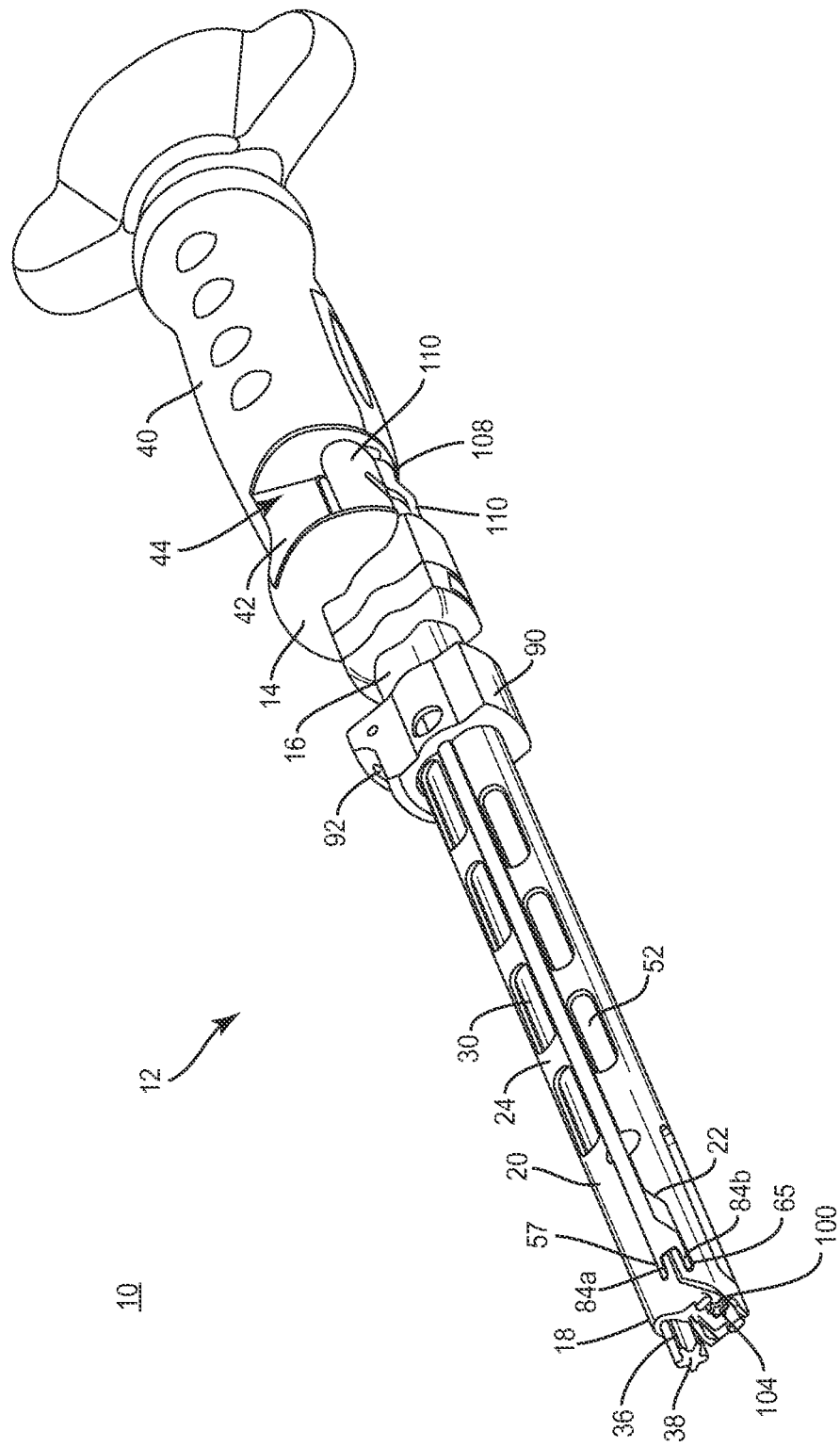
FIG. 1 is a perspective view of components of one embodiment of a surgical system in accordance with the principles of the present disclosure.
Figure 2:
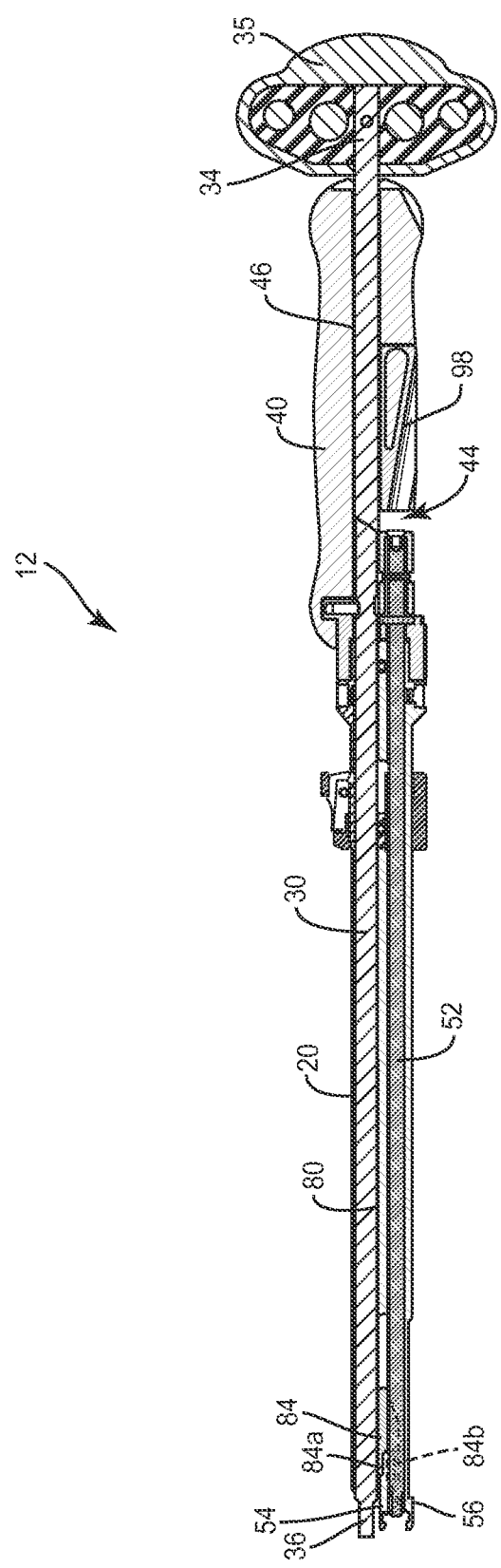
FIG. 2 is a cross section view of the components shown in FIG. 1.

The exemplary embodiments of the surgical system and related methods of use disclosed are discussed in terms of medical devices for the treatment of musculoskeletal disorders and more particularly, in terms of a surgical system for delivering an expandable spinal implant and a method for treating a spine.

In one embodiment, the surgical system includes a surgical instrument including an inserter engageable with a spinal implant. In some embodiments, the surgical system includes a low profile inserter employed with a corpectomy cage. In some embodiments, the low profile inserter interfaces with an expandable corpectomy cage or vertebral body replacement device. In one embodiment, the surgical instrument includes an integrated mechanism to facilitate expansion and collapse of an expandable spinal implant, such as, for example, a corpectomy cage. In one embodiment, the surgical instrument includes an integrated mechanism to facilitate locking the spinal implant. In one embodiment, the surgical instrument includes an integrated mechanism to facilitate locking an interface between the spinal implant and the surgical instrument. In one embodiment, the surgical instrument includes a navigation device to facilitate positioning and/or tracking of components of the surgical system.

In one embodiment, the surgical instrument includes an offset connection with the spinal implant to facilitate insertion during a posterior corpectomy procedure. In one embodiment, the surgical instrument includes a mechanism to connect an expansion shaft with the surgical instrument. In one embodiment, the surgical instrument is configured to expand, collapse and lock the spinal implant with a single instrument. In one embodiment, the surgical instrument includes a gear driven expansion mechanism configured to facilitate precise height adjustments of the spinal implant. In one embodiment, the surgical instrument is manufactured with 17-4 PH stainless steel.

In one embodiment, the surgical instrument includes bilateral tabs configured to connect the spinal implant with the instrument. In one embodiment, the surgical instrument includes two sets of bilateral tabs configured to connect the spinal implant with the instrument. In one embodiment, the surgical instrument includes a pinion configured to drive a rack to adjust the height of the spinal implant.

In one embodiment, the surgical instrument includes a hex driver configured for connection with a locking setscrew on the spinal implant. In one embodiment, the hex driver includes a knob configured to move the hex driver and unlock the hex driver with a push button. In one embodiment, the hex driver includes a shaft having at least one ramp configured to engage and open the tabs. In one embodiment, the hex driver is aligned with a setscrew of the spinal implant and a pinion is aligned with a rack disposed with the spinal implant. In one embodiment, the hex driver is translated into a locked position to engage the tabs with the spinal implant.

In one embodiment, the surgical instrument includes a rotating handle configured to adjust the height of the spinal implant. In one embodiment, rotating the handle clockwise causes an increase in the height of the spinal implant. In one embodiment, rotating the handle counterclockwise causes a decrease in the height of the spinal implant. In one embodiment, the handle drives the pinion through the gear mechanism of the spinal implant. In one embodiment, the gear ratio is 3.5:1.

In one embodiment, the surgical instrument includes a straight, in-line inserter for manual locking. In some embodiments, the surgical instrument includes a release handle configured to facilitate expansion and collapse of the instrument. In one embodiment, the surgical instrument includes spring tabs to facilitate connection with the spinal implant. In one embodiment, the surgical instrument includes a two-stage T-handle. In one embodiment, the surgical instrument includes a push button release handle. In some embodiments, the surgical instrument includes a set screw driver. In some embodiments, the surgical instrument includes a locking mechanism with an auto-lock release.

In one embodiment, one or all of the components of the surgical system are disposable, peel-pack, pre-packed sterile devices that can be used with an implant. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-6, there are illustrated components of a surgical system 10, including a surgical instrument 12 in accordance with the principles of the present disclosure.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

The components of surgical system 10 including surgical instrument 12 can be employed, for example, with mini-open and open surgical techniques to deliver and introduce instrumentation and/or an implant, such as, for example, a corpectomy implant, at a surgical site within a body of a patient, for example, a section of a spine. In one embodiment, system 10 may be employed with surgical procedures, such as, for example, corpectomy and discectomy, which include fusion and/or fixation treatments that employ implants.

Instrument 12 includes a body 14 that extends between an end 16 and an end 18. Body 14 includes a sleeve 20 and a handle 40. Sleeve 20 includes a surface, such as, for example, a tubular housing 22 and a surface, such as, for example, a tubular housing 24. Housing 24 defines a channel 26 configured for disposal of at least a portion of a member, such as, for example, a shaft 30. Channel 26 defines a passageway 32 configured for rotatable disposal of shaft 30.

Shaft 30 extends between an end 34 and an end 36. End 36 includes a pinion gear portion 38 configured for engagement with an interbody implant, as described herein. End 36 extends a distance past end 18 to facilitate engagement with the implant. End 34 extends through handle 40 and includes a rotatable handle 35 configured to rotate shaft 30 such that pinion gear portion 38 engages the implant to expand, contract, collapse and/or extend the implant. In one embodiment, shaft 30 includes a provisional lock to provisionally lock shaft and the implant in a desired orientation.

Handle 40 is configured to facilitate manipulation of instrument 12. Handle 40 includes a surface 42 that defines a cavity 44 configured for disposal of a handle 98 of a driver 52, as described herein. Surface 42 defines a cavity 46 configured for rotatable disposal of shaft 30. End 34 of shaft 30 extends a distance past handle 40 to facilitate engagement with handle 35.

Sleeve 20 includes extensions 54, 56. Extension 54 includes a surface 60 that defines at least one mating element, such as, for example, tabs 62, as described herein. Tabs 62 extend inwardly from surface 60 about a driver 52 to engage the implant, as described herein. Extension 54 includes a cantilever 55 extending into cavity 50 to define a slot 57. Slot 57 is configured to receive a prong to fix extension 54 with extension 56, as described herein.

Extension 56 includes a surface 64 that defines a tab 66. Extension 56 is biased by translation of a slider 80 from an expanded configuration to a mating configuration to releasably attach instrument 12 with the implant, as described herein. Extension 56 includes a tapered portion 68 and an enlarged portion 70. Portion 68 and portion 70 define a surface 72 configured to expand and contract extension 56, as described herein. In one embodiment, surface 72 is angled so as to facilitate movement of extension 56. Extension 56 includes a cantilever 63 extending into cavity 50 to define a slot 65 configured to receive a prong to fix extension 54 with extension 56, as described herein.

Figure 7:
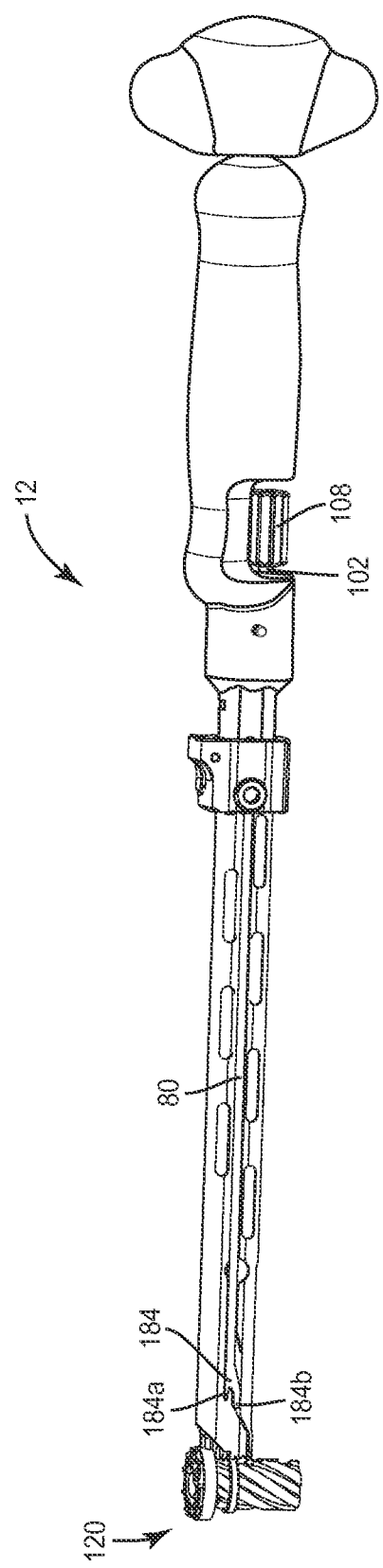
FIG. 7 is a perspective view of components of one embodiment of a surgical system in accordance with the principles of the present disclosure.
Figure 8:
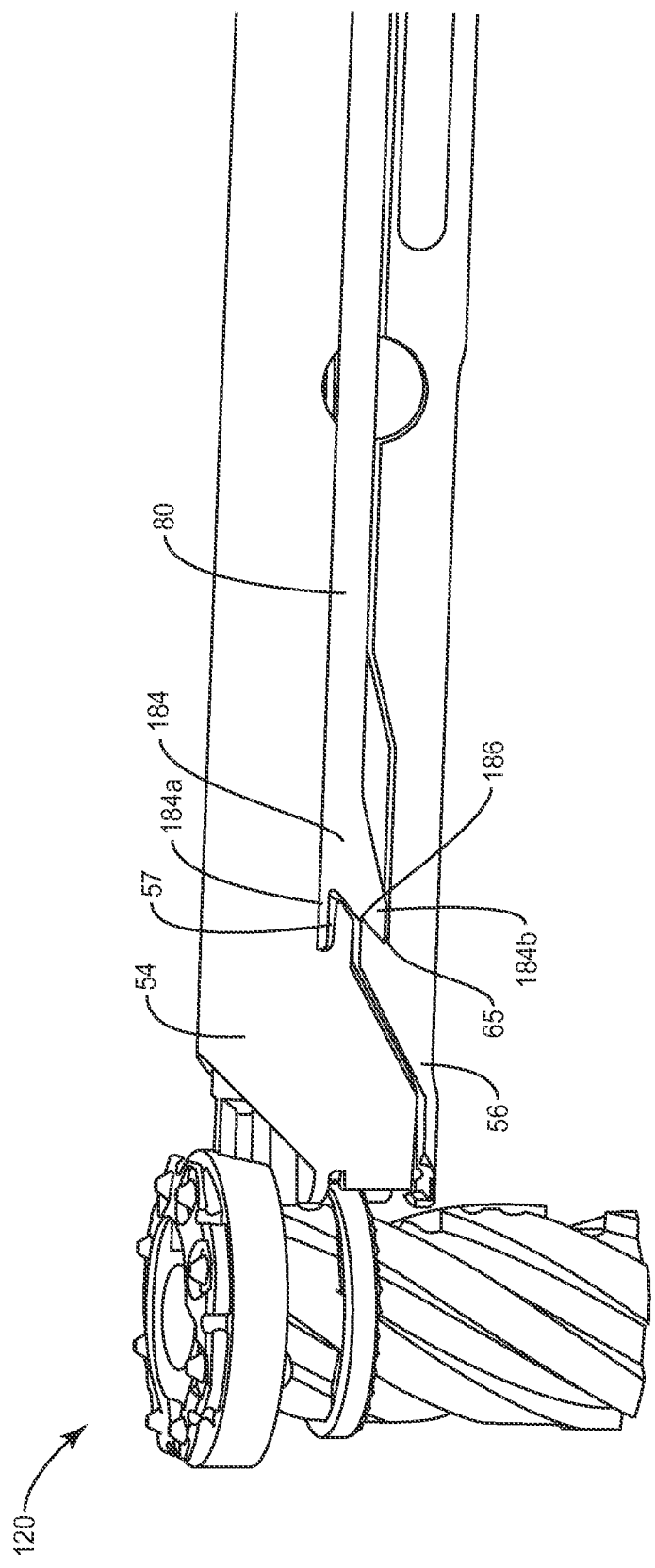
FIG. 8 is an enlarged break away view of components of the system shown in FIG. 7.

A member, such as, for example, a slider 80 is configured for disposal with sleeve 20 between shaft 30 and driver 52. Slider 80 includes a shaft 82 and a bifurcated portion 84. Portion 84 includes a prong 84a configured for disposal with slot 57 and a prong 84b configured for disposal with slot 65. Portion 84 includes a sloped surface 86 configured to engage surface 72. Portion 84 is configured to expand and contract extensions 54, 56 between the expanded configuration and the mating configuration. Translation of slider 80 along extension 56 in one direction causes section 86 to engage surface 72 and translate into tapered portion 68 causing extensions 54, 56 to expand and biases tab 66 outward in the expanded configuration. Translation of slider 80 in an opposite direction causes section 86 to engage surface 72 and translate into enlarged portion 70 causing extension 56 to bias tab 66 inward into the mating configuration and prongs 84a, 84b to engage slots 57, 65 to fix extension 54 with extension 56. In one embodiment, as shown in FIGS. 7 and 8, slider 80 includes a bifurcated portion 184 having a prong 184a and a prong 184b, and a sloped surface 186 therebetween. Prongs 184a, 184b engage slots 57, 65 to fix extension 54 with extension 56.

Slider 80 includes an actuator 90 configured to engage and disengage prongs 84a, 84b from slots 57, 65, as shown in FIGS. 1-6. Actuator 90 is disposed about and translatable along sleeve 20. Actuator 90 includes a button 92 configured for a quick release of slider 80 to engage prongs 84a 84b with slots 57, 65.

Figure 9:
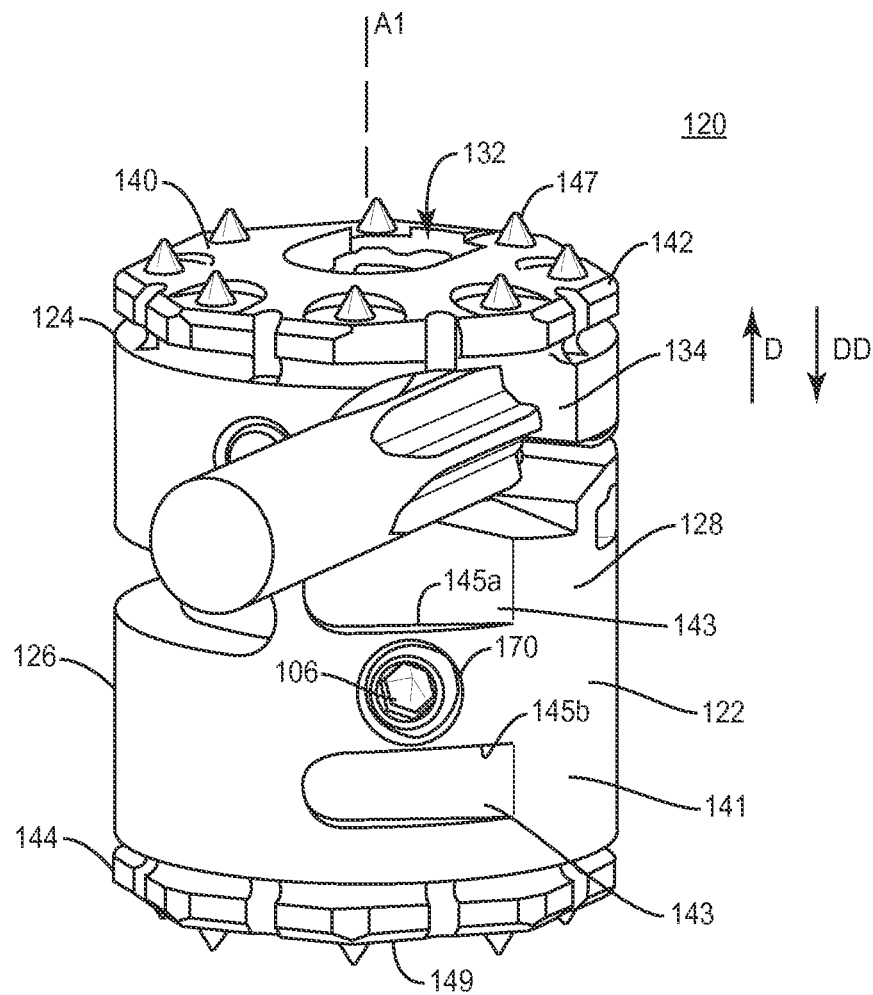
FIG. 9 is a perspective view of components of one embodiment of a surgical system in accordance with the principles of the present disclosure.

Housing 22 defines a channel 50 that defines a passageway 58 configured for moveable disposal of at least a portion of a member, such as, for example, a driver 52, as described herein. Driver 52 extends between an end 100 and an end 102. End 100 includes an engagement portion 104 configured to engage a locking element, such as, for example a set screw 106, as shown in FIG. 9. In some embodiments, engagement portion 104 includes configurations, such as, for example, triangular, square, polygonal, hexalobular, star or torx. End 102 includes a rotatable handle 108 configured to rotate driver 52 such that set screw 106 locks the implant in a fixed configuration. In one embodiment, as shown in FIG. 1, handle 108 includes levers 110 configured to allow toggle and movement of driver 52 to facilitate engagement of set screw 106 with the implant.

System 10 includes an implant, such as, for example, an expandable corpectomy implant 120, as shown in FIG. 9, having a part, such as, for example, an outer body 122 having a tubular configuration. Body 122 extends in a linear configuration and defines a longitudinal axis A1. Body 122 extends between an end 124 and an end 126.

Figure 10:
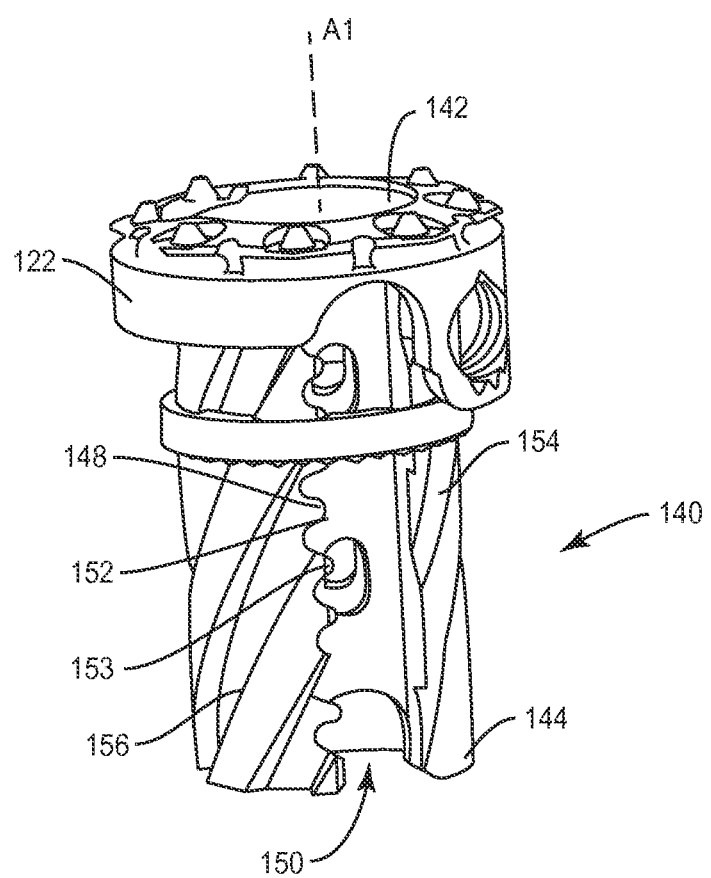
FIG. 10 is a perspective view of components of one embodiment of a surgical system in accordance with the principles of the present disclosure.
Figure 11:
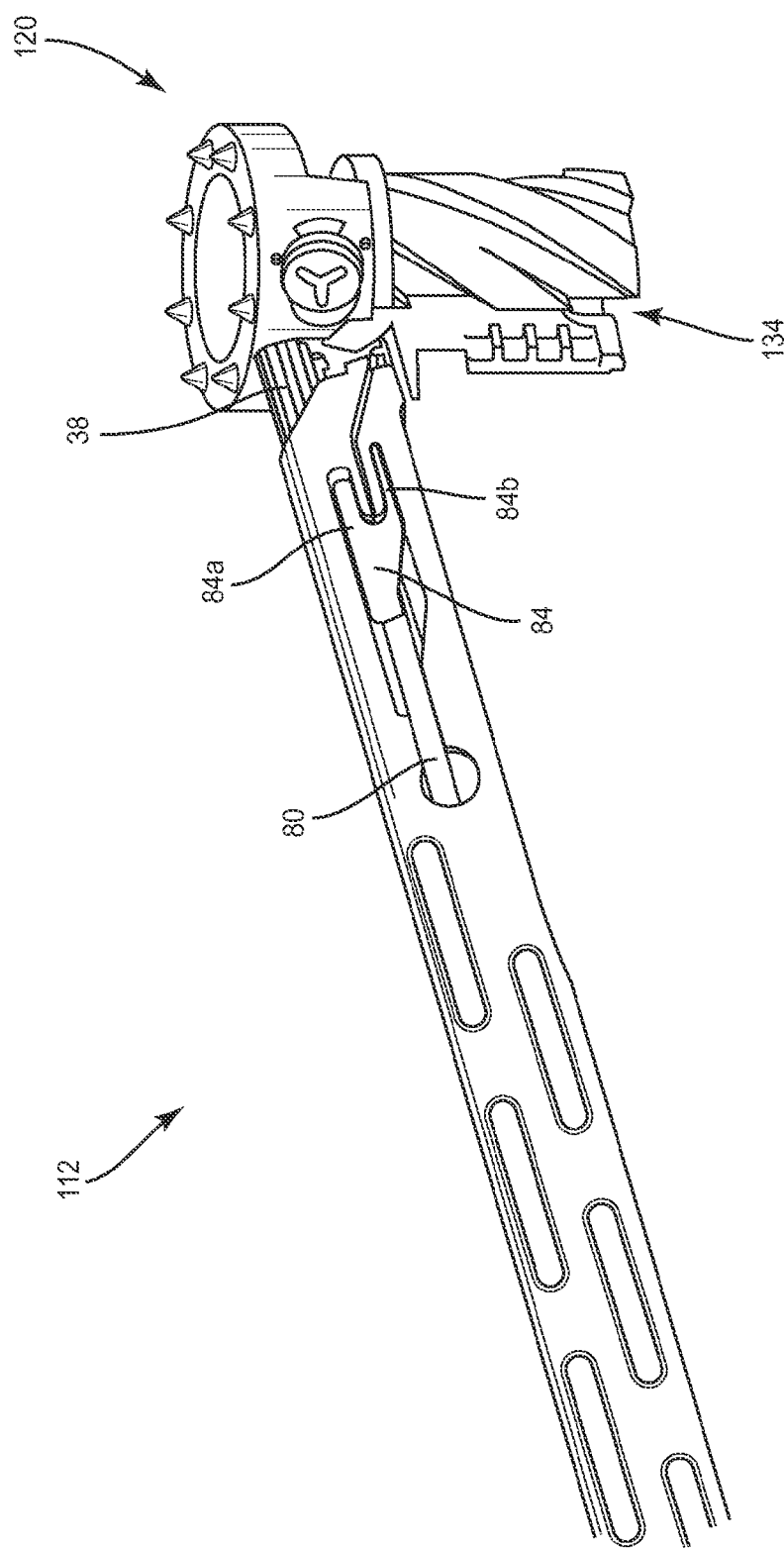
FIG. 11 is a perspective break away view of components of one embodiment of a surgical system in accordance with the principles of the present disclosure.

Body 122 includes a wall, such as, for example, a tubular wall 128. Wall 128 includes an inner surface that defines an axial cavity 132 extending between ends 124, 126 and an outer surface 141. Surface 141 defines a lateral opening 134. Opening 134 is configured for disposal of pinion gear portion 38 to facilitate expansion of body 122 and a part, such as, for example, an inner body 140 of implant 120, as shown in FIG. 10. Surface 141 defines indents 143 configured to receive tabs 62, 66 to connect instrument 12 with implant 120 for insertion into a patient body. Openings 143 defines ledges 145a, 145b configured to matingly engage with tabs 62, 66 to facilitate insertion of implant 120. Surface 141 defines an opening 170 configured to receive set screw 106 to lock body 122 with body 140.

Body 140 has a tubular configuration and is oriented for disposal within axial cavity 132. Body 140 extends in a linear configuration relative to axis A1. Body 140 extends between an end 142 and an end 144. End 142 defines an end face 147 including a substantially planar surface that is configured to engage vertebral tissue. End 144 defines an end face 149 including a substantially planar surface that is configured to engage vertebral tissue. Body 140 is configured for disposal with cavity 132 such that bodies 122, 140 are concentric with axis A1.

Body 140 includes a surface 148 having a gear rack 152 having a plurality of teeth 153 that are disposed therealong. Pinion gear portion 38 is disposed within slot 150 for relative axial translation and rotation such that circumferentially disposed pinion gear portion 38 engages teeth 153. As shaft 30 is rotated, pinion gear portion 38 engages teeth 153 to drive body 140 in an axial direction and cause axial translation of body 140 relative to body 122 to expand or contract implant 120, as described herein.

Body 140 axially translates relative to body 122 and band 158 is disposed therewith between a first, contracted or nested configuration and a second, expanded configuration such that outer body 122 and inner body 140 are disposed to engage adjacent vertebral soft tissue and bone surfaces, as will be described, to restore height and provide support in place of removed vertebrae and/or intervertebral tissue.

In assembly, operation and use, to treat the affected section of vertebrae V, a medical practitioner obtains access to a surgical site including vertebrae V in any appropriate manner, such as through incision and retraction of tissues. In some embodiments, system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, corpectomy is performed for treating the spine disorder. The diseased and/or damaged portion of vertebrae V, and diseased and/or damaged intervertebral discs are removed to create a vertebral space S.

A preparation instrument (not shown) is employed to remove disc tissue, fluids, adjacent tissues and/or bone, and scrape and/or remove tissue from endplate surfaces E1 of vertebrae V1 and/or endplate surface E2 of vertebrae V2. Implant 120 is provided with at least one agent, similar to those described herein and as described above, to promote new bone growth and fusion to treat the affected section of vertebrae V.

Figure 12:
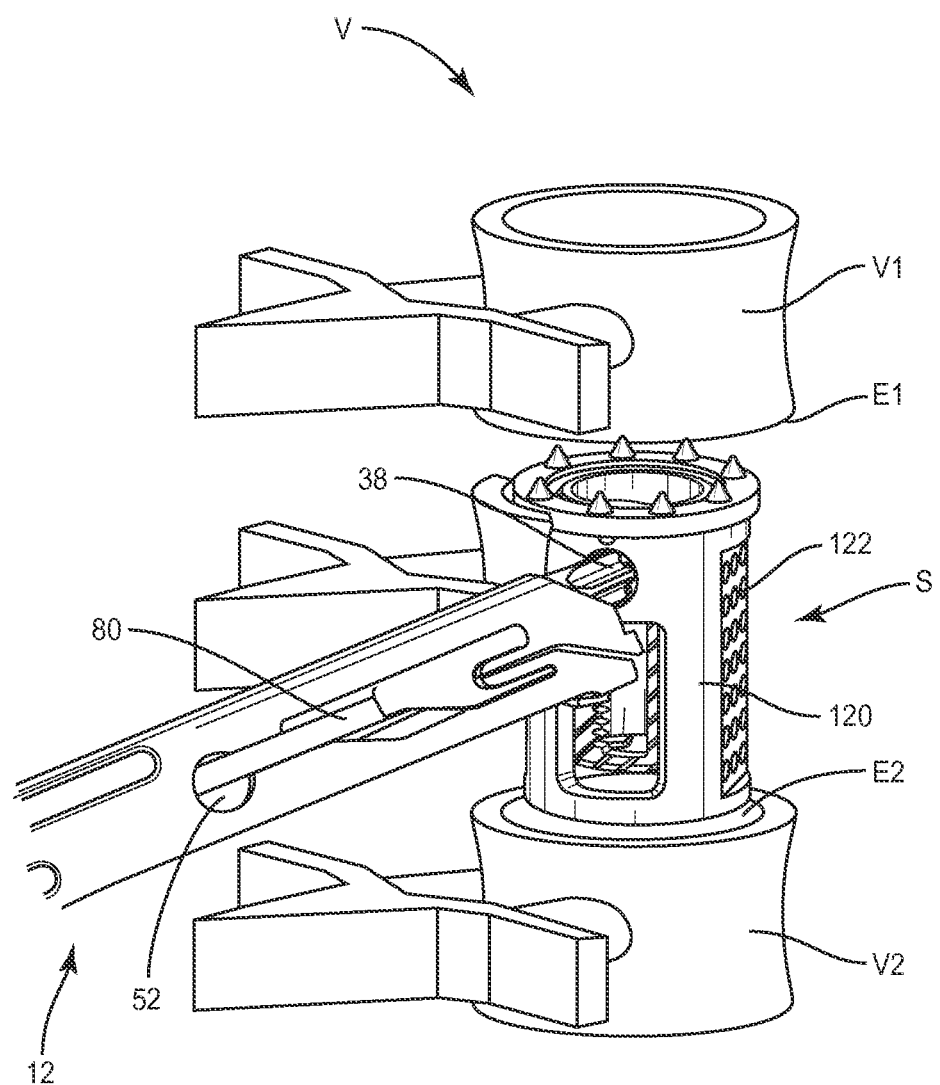
FIG. 12 is a perspective view of components of one embodiment of a surgical system in accordance with the principles of the present disclosure disposed with vertebrae.

Implant 120 is disposed in a first orientation, as shown in FIG. 12, such that body 122 and body 140 are disposed in a concentric configuration with longitudinal axis A1 and disposed in a telescopic arrangement for delivery and implantation adjacent a surgical site. Bodies 122, 140 are seated concentrically such that substantially all of inner body 140 is disposed within outer body 122 in a nested configuration. Driver 52 is connected with set screw 106. Shaft 30 is aligned with opening 134 such that pinion gear portion 38 is aligned with gear teeth 153 of body 140. Tabs 62 are engaged with implant 120. Actuator 90 is translated, in the direction shown by arrow A in FIG. 4a, to a position at end 16 of sleeve 20, such that prongs 84a, 84b are disengaged from slots 57, 65 to allow extension 56 to flex, in the direction shown by arrow B in FIG. 4b, to facilitate engagement of tab 66 with ledge 145b.

Once tab 66 is positioned with ledge 145b, button 92 is pressed to translate slider 80, in the direction shown by arrow AA in FIG. 5a, into the closed position such that prongs 84a, 84b are engaged with slots 57, 65 and tab 66 engages ledge 145b by movement of extension 56, in the direction shown by arrow BB in FIG. 5b, for a rigid connection between instrument 12 and implant 120.

Figure 3:
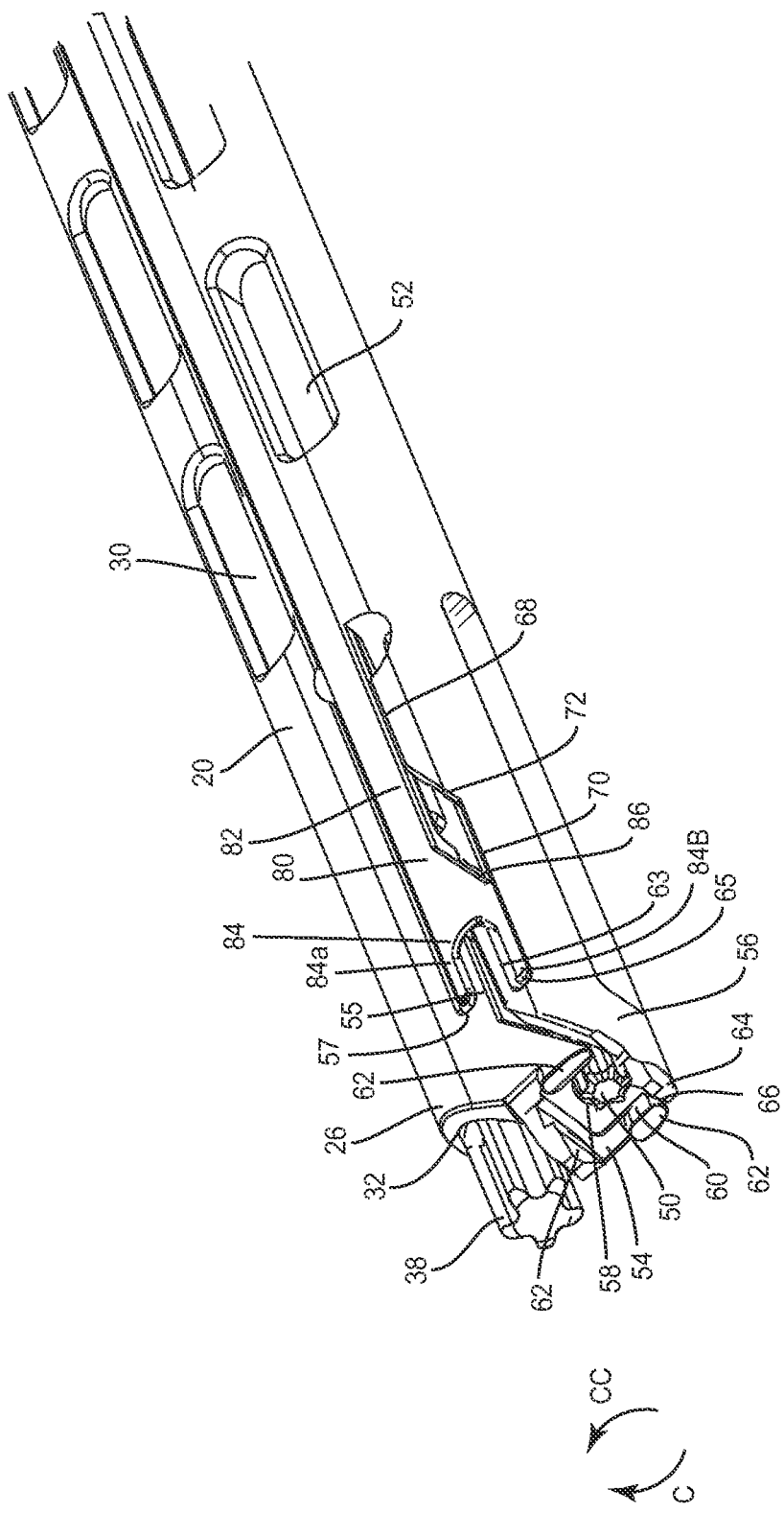
FIG. 3 is an enlarged break away view of the components shown in FIG. 1.

Shaft 30 is rotated via manipulation of handle 40, in the direction shown by arrow C in FIG. 3, such that pinion gear portion 38 of shaft 30 engages teeth 153 for axial translation of body 140 relative to body 122. As shaft 30 is rotated in the direction shown by arrow C, pinion gear portion 38 engages teeth 153 to drive body 140 in an axial direction, as shown by arrow D in FIG. 13 and cause axial translation of body 140 relative to body 122 to expand implant 120. In one embodiment, shaft 30 is rotated in a direction shown by arrow CC in FIG. 3 such that pinion gear portion 38 engages teeth 153 to drive body 140 in an axial direction, as shown by arrow DD in FIG. 13, and cause axial translation of body 140 relative to body 122 to contract and/or collapse implant 120 from an expanded configuration.

Figure 13:
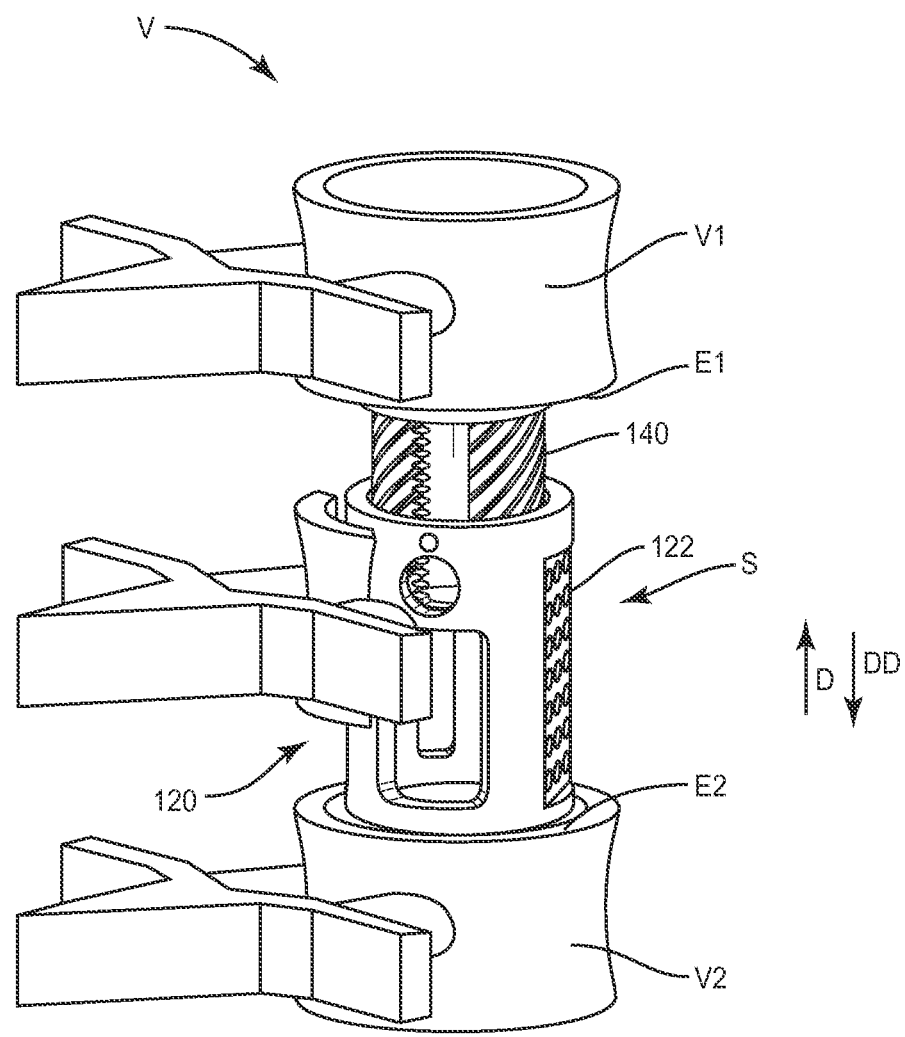
FIG. 13 is a perspective view of components of one embodiment of a surgical system in accordance with the principles of the present disclosure disposed with vertebrae.

As shaft 30 is rotated, body 140 axially translates, in the direction shown by arrow D in FIG. 13, relative to body 122 such that band 158 slidably rotates within cavity 136 to facilitate expansion of implant 120 via engagement with a gear surface 156 of body 140, as shown in FIG. 10. Body 140 axially translates relative to body 122 to a second, expanded orientation such that outer body 122 and inner body 140 are disposed to engage adjacent vertebral soft tissue and bone surfaces, as will be described, to restore height and provide support in place of removed vertebrae and/or intervertebral tissue. Driver 52 is aligned with opening 170 via manipulation of handle 108 such that set screw 106 engages body 140 to lock body 140 relative to body 122 in a selected configuration and/or fixed position.

In one embodiment, implant 120 may include fastening elements, which may include locking structure, configured for fixation with vertebrae V1, V2 to secure joint surfaces and provide complementary stabilization and immobilization to a vertebral region. In some embodiments, the locking structure may include fastening elements such as, for example, rods, plates, clips, hooks, adhesives and/or flanges. In some embodiments, system 10 can be used with screws to enhance fixation.

In one embodiment, system 10 includes an agent, which may be disposed, packed, coated or layered within, on or about the components and/or surfaces of system 10. In some embodiments, the agent may include bone growth promoting material, such as, for example, bone graft to enhance fixation of the components and/or surfaces of system 10 with vertebrae V. In some embodiments, the agent may include one or a plurality of therapeutic agents and/or pharmacological agents for release, including sustained release, to treat, for example, pain, inflammation and degeneration.

Upon completion of the procedure, the surgical instruments, assemblies and non-implanted components of system 10 are removed and the incision is closed. The components of system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of system 10. In some embodiments, system 10 may include one or a plurality of plates, connectors and/or bone fasteners for use with a single vertebral level or a plurality of vertebral levels.

In one embodiment, as shown in FIGS. 14-17, a system 210, similar to system 10 and the methods described herein, includes an instrument 212, similar to instrument 12 and an implant 120, as described herein. Instrument 212 includes a body 214 that extends between an end 216 and an end 218. Body 214 includes a sleeve 220 and a handle 240. Sleeve 220 includes a tubular housing 222 and a tubular housing 224. Housing 222 defines a channel 226 configured for rotatable disposal of a shaft 230.

Shaft 230 extends between an end 234 and an end 236. End 236 includes a pinion gear portion 238 configured for engagement with interbody implant 120. End 234 extends through handle 240 and includes a rotatable handle 270, as described herein. Handle 270 is configured to rotate shaft 230 such that pinion gear portion 238 engages implant 120 to expand, contract, collapse and/or extend the implant.

Figure 14:
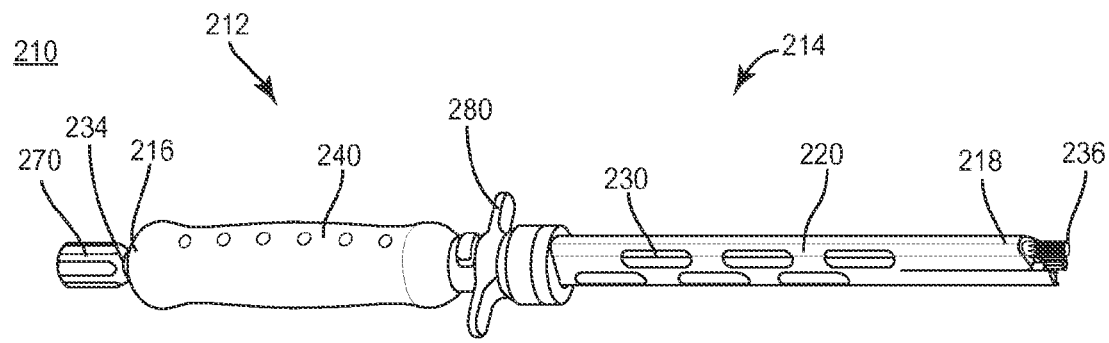
FIG. 14 is a perspective view of components of one embodiment of a surgical system in accordance with the principles of the present disclosure.
Figure 15:
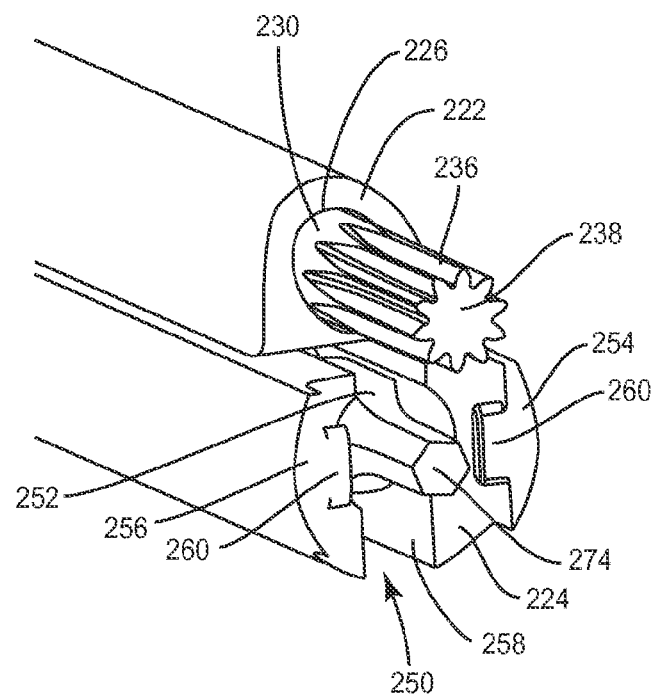
FIG. 15 is an enlarged break away view of components of the system shown in FIG. 14.
Figure 16:
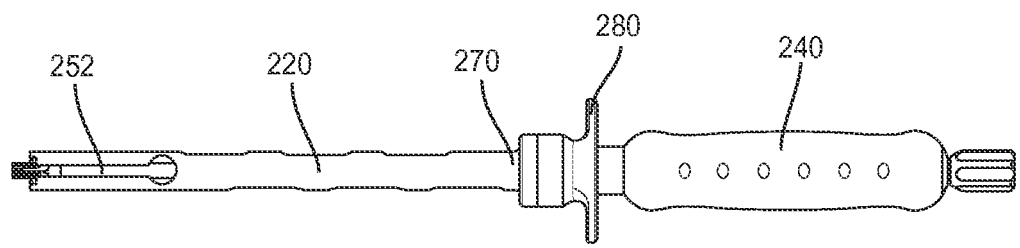
FIG. 16 is a side view of components of one embodiment of a surgical system in accordance with the principles of the present disclosure.
Figure 17:
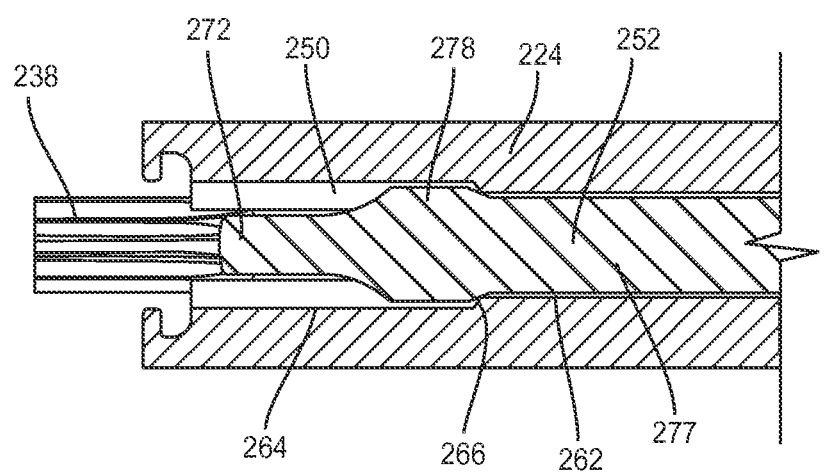
FIG. 17 is an enlarged break away view of components of the system shown in FIG. 15.

Housing 224 defines a channel 250 configured for moveable disposal of a driver 252, as described herein. Housing 222 includes extension 254 and extension 256. Extensions 254, 256 form a mating surface 258 that defines at least one mating element, such as, for example, at least one tab 260, as described herein. As shown in FIG. 14, tabs 260 include a pair of opposing tabs 260 oriented bilaterally. Tabs 260 extend from surface 258 inwardly into channel 250 to engage implant 120. Extensions 254, 256 are configured such that extensions 254, 256 are biased from an expanded configuration to a mating configuration to releasably attach tabs 260 with implant 120, as described herein. As shown in FIG. 17, channel 250 includes a reduced diameter portion 262 and an enlarged portion 264. Portion 262 and portion 264 define a surface 266 configured to cause extensions 254, 256 to expand when engaged with driver 252, as described herein. In one embodiment, surface 266 is angled so as to facilitate movement of extensions 254, 256.

Driver 252 extends between an end 270 and an end 272. End 272 includes an engagement portion 274 configured to engage a set screw. Driver 252 includes a shaft 277 having an enlarged portion 278 configured for engagement with surface 266 of channel 250, as described herein. End 270 includes a rotatable handle 280 configured to rotate driver 252 such that a set screw locks implant 120 in a selected fixed configuration, similar to that described herein.

Translation of driver 252 along channel 250 in one direction, as shown by arrow K in FIG. 17, causes portion 278 to engage surface 266 and translate in portion 262 such that extensions 254, 256 expand and bias tabs 260 outward into an expanded configuration. Translation of driver 252 in an opposite direction, as shown by arrow L in FIG. 17, causes portion 278 to engage surface 266 and translate into portion 264 causing extensions to bias tabs 260 inward into a mating configuration with implant 120, similar to that described herein.

Figure 18:
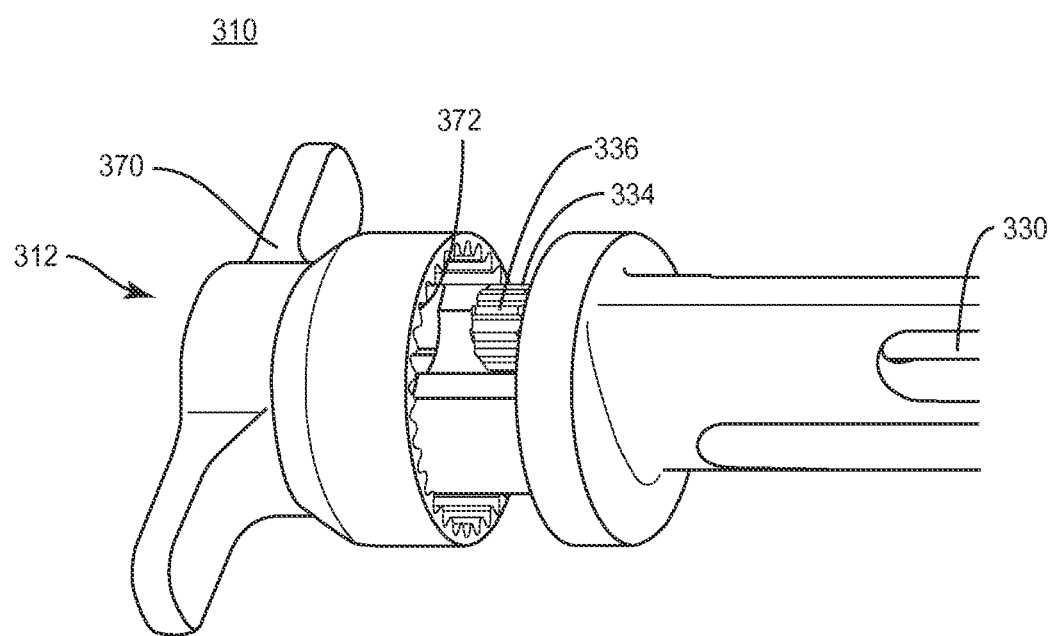
FIG. 18 is a perspective view of components of one embodiment of a surgical system in accordance with the principles of the present disclosure.

In one embodiment, as shown in FIG. 18, a system 310, similar to the systems and methods described herein, includes an instrument 312, similar to instrument 12 and an implant 120, as described herein. A shaft 330 includes an end 334 that includes a pinion gear portion 336. Shaft 330 is engageable with a rotatable handle 370. Handle 370 includes a geared surface 372 configured to engage pinion gear portion 336 to rotate shaft 330 such that implant 120 incrementally expands, contracts, collapses and/or extends. In one embodiment, rotating handle 370 clockwise causes implant 120 to increase in height. In one embodiment, rotating handle 370 counter-clockwise causes implant 120 to decrease in height. In one embodiment, a gear ratio between pinion gear portion 336 and gear surface 372 is 3.5:1.

Figure 19:
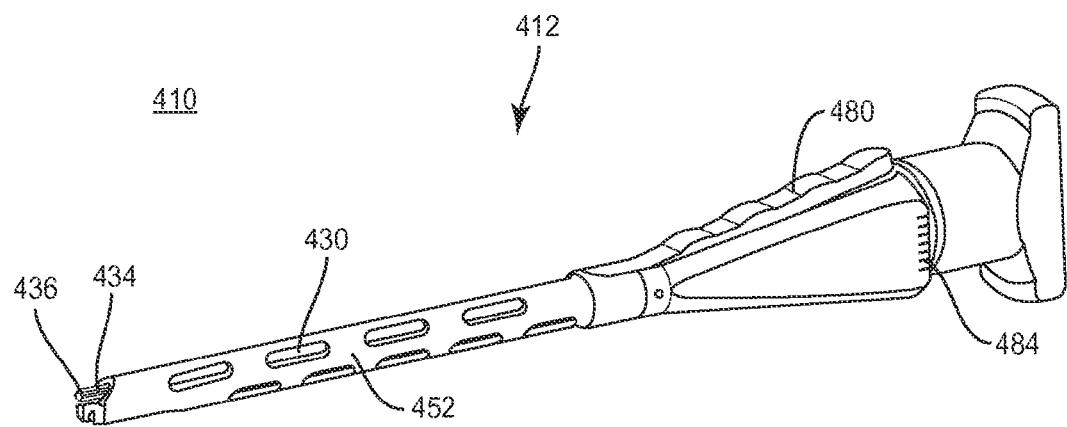
FIG. 19 is a perspective view of components of one embodiment of a surgical system in accordance with the principles of the present disclosure.
Figure 20:
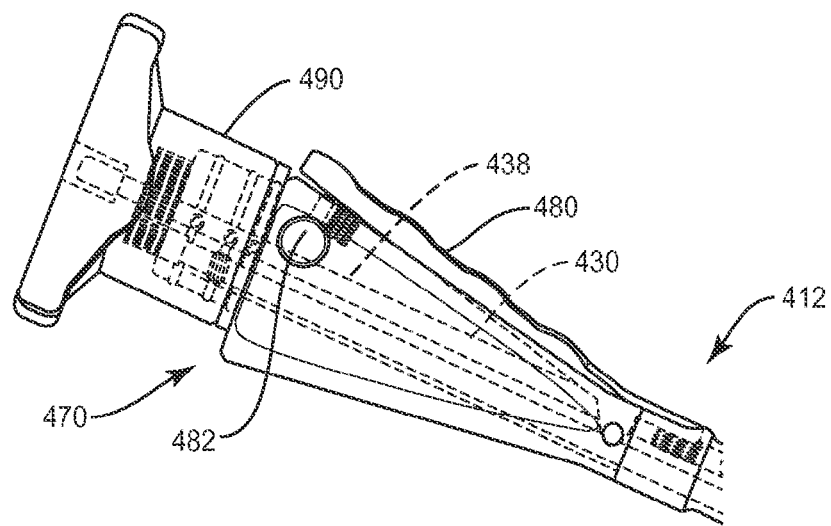
FIG. 20 is an enlarged break away view of components of the system shown in FIG. 19.

In one embodiment, as shown in FIGS. 19 and 20, a system 410, similar to the systems and methods described herein, includes an instrument 412, similar to instrument 12 and an implant 120, as described herein. A low profile shaft 430 includes an end 434 that includes a pinion gear portion 436. An end 438 of shaft 430 is engageable with a handle 470. Handle 470 includes a release button 480 configured to facilitate incremental expansion and collapse of implant 120 via each depression of button 480. Handle 470 includes a button 482 configured to release shaft 430 from implant 120. In one embodiment, button 482 is disposed on a side of handle 470. In one embodiment, handle 470 includes indicia 484 to indicate the height of implant 120 during expansion and/or collapse.

Instrument 412 includes a handle, such as for example, a two-stage T-handle 490 engaged with a driver 452 and shaft 430. Handle 490 is configured to incrementally rotate driver 452 to facilitate locking of implant 120. Handle 490 is configured to rotate shaft 430 in lieu of pressing button 480 for incremental expansion and/or collapse of implant 120.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a body extending between a first end and a second end including at least one mating element engageable with an interbody implant, the body comprising a first extension having a first slot and a second extension having a second slot;

a first member disposed within the first extension and engageable with the interbody implant to move the interbody implant between a first configuration and a second, expanded configuration;

a second member disposed within the second extension and engageable with the interbody implant to fix the interbody implant in the second configuration; and a slider that is movable along the body between a first orientation in which prongs of the slider are disposed in the slots and the first extension is fixed relative to the second extension and a second orientation in which the prongs are disengaged from the slots and the first extension is movable relative the second extension.

2. A surgical instrument as recited in claim 1, wherein the body includes a handle and a sleeve that defines at least one inner cavity for disposal of at least a portion of each of the members.

3. A surgical instrument as recited in claim 1, wherein the at least one mating element includes two bilateral tabs.

4. A surgical instrument as recited in claim 1, wherein the at least one mating element includes four tabs.

5. A surgical instrument as recited in claim 4, wherein the four tabs are disposed about the second member.

6. A surgical instrument as recited in claim 1, wherein the first member includes a pinion gear shaft engageable with teeth of the interbody implant.

7. A surgical instrument as recited in claim 1, wherein the first member includes a rotatable handle.

8. A surgical instrument as recited in claim 1, wherein the first member includes a handle comprising a provisional lock.

9. A surgical instrument as recited in claim 1, wherein the second member includes a driver engageable with a set screw of the interbody implant.

10. A surgical instrument as recited in claim 1, wherein the second member includes a rotatable handle.

11. A surgical instrument as recited in claim 1, wherein the at least one mating element is biased from an expanded configuration to a mating configuration.

12. A surgical instrument as recited in claim 1, wherein the second member is engageable with the at least one mating element to fix the interbody implant in the second configuration.

13. A surgical implant system comprising:
a body extending between a first end and a second end engageable with an interbody implant, the body comprising a first extension having a first slot and a second extension having a second slot, the interbody implant comprising a first part including a wall that defines an axial cavity and at least one lateral opening configured for disposal of the at least one mating element and a second part configured for disposal with the axial cavity and including a wall having an axial surface disposed along a thickness thereof, the axial surface defining at least a portion of an axial opening and including a plurality of gear teeth disposed therealong, wherein the first part is engageable with the teeth to axially translate the second part of the implant relative to the first part;
a first member disposed within the first extension and engageable with the first part to move the interbody implant between a first configuration and a second, expanded configuration;
a second member disposed within the second extension and engageable with the interbody implant to fix the interbody implant in the second configuration; and
a slider that is movable along the body between a first orientation in which prongs of the slider are disposed in the slots and the first extension is fixed relative to the second extension and a second orientation in which the prongs are disengaged from the slots and the first extension is movable relative the second extension.

14. A surgical instrument as recited in claim 13, wherein the second end includes at least one mating element engageable with the first part.

15. A surgical instrument as recited in claim 14, wherein the at least one mating element includes four tabs disposed about the second member.

16. A surgical instrument as recited in claim 13, wherein the first member includes a pinion gear shaft engageable with teeth of the interbody implant.

17. A surgical instrument as recited in claim 13, wherein the first member includes a rotatable handle.

18. A surgical instrument as recited in claim 13, wherein the second member includes a driver engageable with a set screw of the interbody implant.

19. A surgical instrument as recited in claim 13, wherein the second end includes at least one mating element engageable with the first part, the at least one mating element being biased from an expanded configuration to a mating configuration.

20. A surgical implant system comprising:
a body extending between a first end and a second end including at least one tab engageable with an interbody implant, the body comprising a first extension having a first slot and a second extension having a second slot, the interbody implant comprising:
a first part defining a longitudinal axis and including a wall that defines an axial cavity and at least one lateral opening configured for disposal of the at least one tab; and
a second part configured for disposal with the axial cavity and including a wall having an axial surface disposed along a thickness thereof, the axial surface defining at least a portion of an axial opening and including a plurality of gear teeth disposed therealong, wherein the first part is engageable with the teeth to axially translate the second part relative to the first part,
a first member disposed within the first extension and engageable with the gear teeth to move the implant between a first configuration and a second, expanded configuration;
a second member disposed within the second extension and engageable with a set screw to fix the implant in the second configuration; and
a slider that is movable along the body between a first orientation in which prongs of the slider are disposed in the slots and the first extension is fixed relative to the second extension and a second orientation in which the prongs are disengaged from the slots and the first extension is movable relative the second extension.

* * * * *

UNITED STATES PATENT AND TRADEMARK OFFICE
CERTIFICATE OF CORRECTION

PATENT NO.       : 9,681,961 B2
APPLICATION NO.  : 14/450038
DATED            : June 20, 2017
INVENTOR(S)      : Prevost et al.

It is certified that error appears in the above-identified patent and that said Letters Patent is hereby corrected as shown below:

On the Title Page

In Item (72), under "Inventors", in Column 1, Line 2, delete "Browning," and insert -- Browing, --, therefor.

In the Specification

In Column 4, Line 25, delete "dearly" and insert -- clearly --, therefor.

In Column 9, Line 10, delete "dips," and insert -- clips, --, therefor.

In the Claims

In Column 11, Line 13, in Claim 1, delete "relative the" and insert -- relative to the --, therefor.

In Column 12, Line 10, in Claim 13, delete "relative the" and insert -- relative to the --, therefor.

In Column 12, Line 11, in Claim 14, delete "surgical instrument" and insert -- surgical implant system --, therefor.

In Column 12, Line 14, in Claim 15, delete "surgical instrument" and insert -- surgical implant system --, therefor.

In Column 12, Line 17, in Claim 16, delete "surgical instrument" and insert -- surgical implant system --, therefor.

In Column 12, Line 20, in Claim 17, delete "surgical instrument" and insert -- surgical implant system --, therefor.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,681,961 B2

In Column 12, Line 22, in Claim 18, delete "surgical instrument" and insert -- surgical implant system --, therefor.

In Column 12, Line 25, in Claim 19, delete "surgical instrument" and insert -- surgical implant system --, therefor.

In Column 12, Line 48, in Claim 20, delete "part," and insert -- part; --, therefor.

In Column 12, Line 62, in Claim 20, delete "relative the" and insert -- relative to the --, therefor.